United States Patent [19]

Rosenberg

[11] 4,177,149

[45] Dec. 4, 1979

[54] FILTER ASSEMBLY FOR INTRAVENOUS LIQUID ADMINISTRATION APPARATUS

[75] Inventor: David J. Rosenberg, Glen Cove, N.Y.

[73] Assignee: Pall Corporation, Glen Cove, N.Y.

[21] Appl. No.: 926,766

[22] Filed: Jul. 21, 1978

[51] Int. Cl.² ............................................. C02C 1/14
[52] U.S. Cl. .................................... 210/436; 55/158; 55/159; 210/472; 210/500 M
[58] Field of Search ................ 55/159, 185, 522, 524, 55/307, 321–324, 158; 210/433 R, 433 M, 120, 472, 500 M, 436, DIG. 23; 128/214 R

[56] References Cited

U.S. PATENT DOCUMENTS

| 3,523,408 | 8/1970 | Rosenberg | 55/159 |
| 3,631,654 | 1/1972 | Riely | 55/324 |
| 3,650,093 | 3/1972 | Rosenberg | 55/159 |
| 4,013,072 | 3/1977 | Jess | 210/436 |

*Primary Examiner*—Frank Sever

[57] ABSTRACT

A filter for intravenous liquid administration is provided having a filter housing; a filter chamber in the housing; an inlet member and an outlet member in the housing in fluid flow communication with the filter chamber; a filter in the filter chamber disposed across the line of fluid flow through the chamber from the inlet member to the outlet member so that all through flow must pass through the filter; and dividing the chamber into two portions, one upstream and one downstream of the filter; a vent in the housing in flow communication with the upstream portion of the filter chamber; and a liquid-impermeable gas-permeable porous member disposed across the line of flow through the vent, so that all vent flow must pass through the member, the member restricting such flow to gas to which it is permeable; the inlet member being shaped for attachment to a supply of liquid for intravenous administration; and the outlet member being shaped for attachment to an intravenous liquid administration apparatus.

8 Claims, 3 Drawing Figures

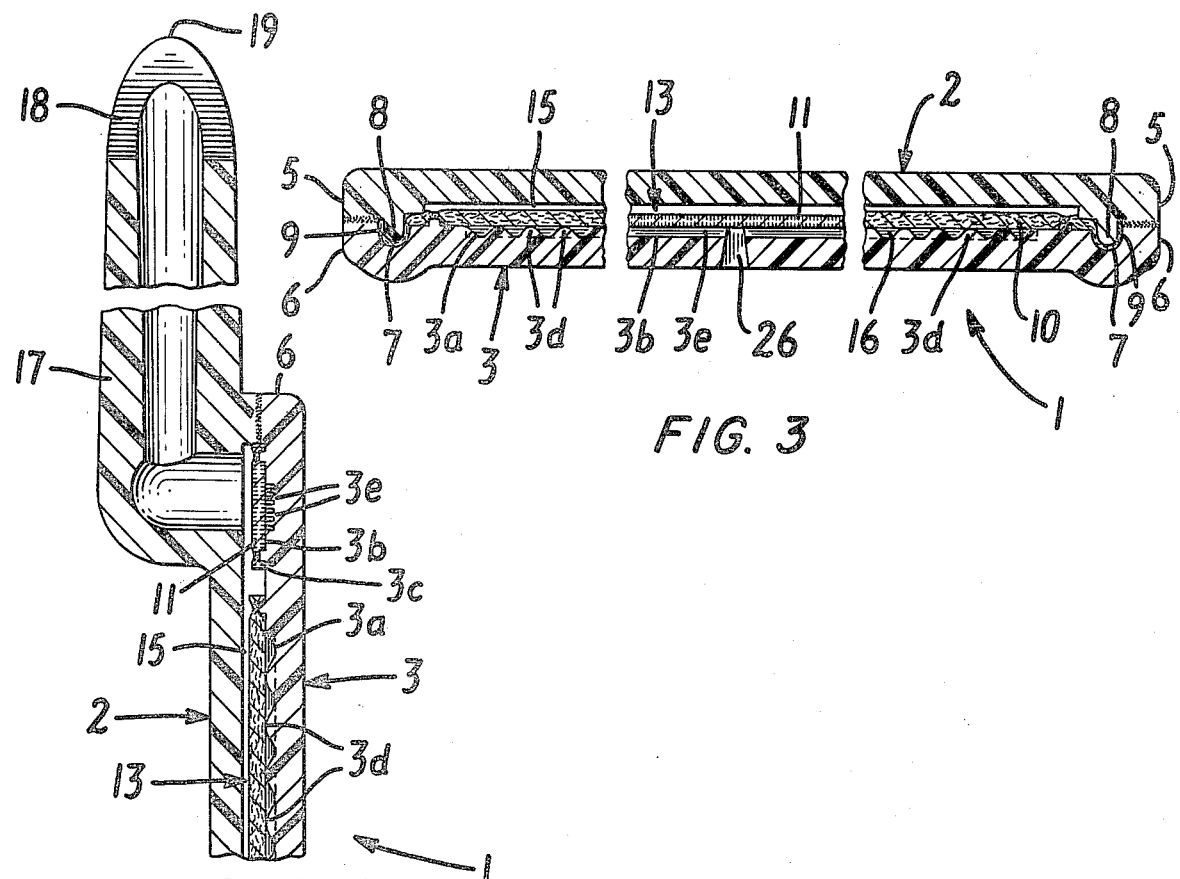
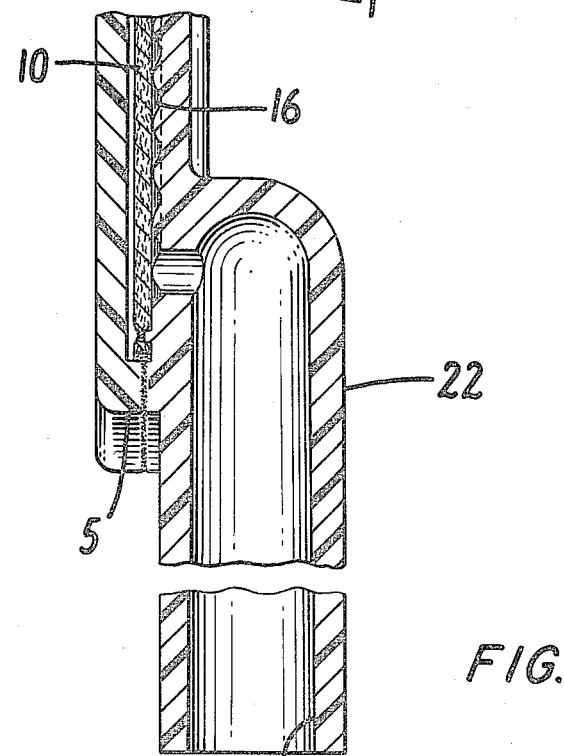
FIG. 3
FIG. 2

FILTER ASSEMBLY FOR INTRAVENOUS LIQUID ADMINISTRATION APPARATUS

In many types of medical treatment, such as blood transfusions, intravenous feeding, and the like, it is necessary to introduce liquids into a patient, sometimes in rather large amounts. When this is done, it is quite important that absolutely no contaminant be permitted to pass into the patient with the liquid, because of the danger of injury or infection, or of an embolism, with possibly fatal consequences. Before such an injection usually can be carried forward, therefore, it is necessary to clear the line of air, and exclude air from the system thereafter. This is not easy to do, however; there is always the danger that air can enter the system during administration, since the system can hardly be easily assembled and disassembled, and still be completely airtight, and there is also the possibility of human error in such assembly. The danger increases if a large volume of fluid is to be injected. If the reservoir runs dry, there is also again a danger that air will be injected. These are especially dangerous problems when the liquid is being injected under pressure, using, for instance, a mechanical pump.

Intravenous liquid administration apparatus accordingly requires a filter to ensure that undesirable or foreign contaminants in gaseous or particulate form not be administered intravenously, with untoward consequences. Many types of intravenous liquid filter assemblies have been provided, of which the system described in Barr et al U.S. Pat. No. 3,557,786 patented Jan. 26, 1971 is exemplary. The filter is usually disposed in an intravenous liquid drip chamber attached to the supply of liquid to be administered, in such a manner that the filter is integral with the chamber housing, all flow through the chamber having to pass through the filter before it can be administered. Such filter assemblies are intended to be disposed of after one use, and to meet the requirement of disposability, the device must be simple and inexpensive to manufacture.

A filter having small pores is incapable of passing gases at fluid pressures below the so-called bubble point of the material, when the filter is wetted by the liquid. The bubble point is defined as the characteristic pressure at which the first bubble of air appears when a filter material is pressurized with air, while immersed just under the surface of the liquid. The bubble point effect is described in U.S. Pat. No. 3,007,334, dated Nov. 7, 1961, and makes it possible to determine the maximum pore size of filter elements, since the air pressure at the bubble point can be directly correlated with the pore size of the filter.

It is apparent that if a filter saturated with fluid is interposed in the line leading from a liquid supply to a patient, air cannot pass along the line beyond the filter, so long as the fluid pressure is below the bubble point of the filter. Such devices have therefore been proposed to prevent the accidental passage of air to patients. However, the problem with such devices is that although they block the passage of air they do not vent it, with the result that the air held back by the filter can cover the surface of the filter, restricting flow, or even blocking it, if the surface is completely covered with air, at the same time increasing the pressure drop across the filter, with the resultant danger that the bubble point of the filter can be reached sooner than expected, after which the blocked air can pass through virtually all at once. The presence of the filter also makes it impossible to clear the line of air, after the filter has once been wetted, and therefore the filter must be dried, before the line can be used again, so that it can be cleared of air before the next use. This, however, is a problem, particularly if the filter must be steam-sterilized or hot water-sanitized before use.

The problem is particularly troublesome with microporous filter material having pores of less than one micron in diameter. Such filters are intended to filter out harmful micro-organisms from fluids, but in such filters, the pressure differential needed to force air through the filter wetted with liquid can be as high as 30 p.s.i.d., as a result of which, complete filter blockage can result from the presence of air in sufficient quantities in the system to cover the surface of the filter.

The impermeability to gas of the wetted filter medium poses serious problems in many applications. Thus, prior to the administration of intravenous liquids, it is necessary to remove all air from the equipment.

A further difficulty with such filters has been the clumsy mode of connection to the supply of liquid to be administered intravenously and to the intravenous administration set or apparatus. The drip chamber assembly described in U.S. Pat. No. 3,557,786, for example, has tubing connections, which require special connectors at both inlet and outlet.

Keedwell U.S. Pat. No. 3,520,416, patented July 14, 1970 provides microporous materials suitable for use as filter media that are capable of passing liquids at low differential pressure while at the same time passing gases even though the materials are wet with or even saturated with a liquid. This unusual characteristic is obtained by providing two kinds of pores through the material, one kind that are preferentially wetted by the liquid, and one kind that are not, and as a consequence do not absorb enough liquid to be plugged with liquid, and therefore are available for passage of gas therethrough.

Riely and Skyles U.S. Pat. No. 3,631,654, patented Jan. 4, 1972, proposed to avoid the gas blockage problem by providing a gas purge device including a filter element that contains both liquid-wetted and liquid-repellent parts, interposed across and screening separate outlets for liquid and gas. The liquid-gas parts will pass the liquid, and the liquid-repellent parts will not be wetted by liquid, and will therefore remain open for passage of gas therethrough. The liquid-wetted and liquid-repellent parts open into separate outlet, the outlet downstream of the liquid-repellent part being a gas outlet, and the outlet downstream of the liquid-wetted part being the delivery passage for gas-free liquid from the device. In this way, the device is capable of separating gases and liquids, and of either venting the gas or delivering it to a gas collection device, while at the same time providing a gas-free supply of liquid. Blockage of the system by the buildup of a gas lock is avoided, while at the same time the entrained gas is entirely eliminated from the liquid. Thus, the device of the invention is particularly adapted for medical applications, where air must be vented from the line, and must also be absolutely prevented from reaching a patient receiving an injection of the liquid. In a preferred embodiment, the filter employed has pores less than about 0.5 micron. If harmful microorganisms are to be filtered out from the fluid, the pores preferably should be less than about 0.3 micron, and then both the liquid and the gas passing through the device are sterilized at the same time. The device has the further advantage that the liquid-wetted or hydrophilic and liquid-repellent or hydrophobic parts can both be provided on the same filter element, thus facilitating servicing, and simplifying the construction.

The gas purge device in accordance with the invention comprises, in combination, a housing, an inlet in the housing for flow of fluid thereinto comprising gas and liquid, an outlet for delivery of liquid-free gas from the housing, and at least one filter element interposed across and screening both the gas and the liquid outlets. There is a liquid-repellent filter or part thereof interposed across and screening the gas outlet, and a liquid-wetted filter, or part thereof, interposed across and screening the liquid outlet, such that only gas can pass from the inlet through the filter into the gas outlet, and only liquid can pass from the inlet through the filter into the liquid outlet. Both the liquid-wetted and liquid-repellent filters preferably have a pore size less than about 0.3 micron, at which harmful micro-organisms cannot pass through, and both are preferably portions of the same filter elements. The housing and associated parts of the gas purge device are preferably made of plastic, and are bonded or fused together in a one-piece construction. The filter element can be fixed therein, so that the entire unit is disposed of when the element needs replacement, or can be removably positioned in the housing for easy replacement when needed.

This device is to be used in conjunction with a drip chamber of conventional type, and the problem is, that this requires two devices instead of one, with resultant increased expense.

A similar device is provided by Rosenberg U.S. Pat. No. 3,523,408, patented Aug. 11, 1970.

The Rosenberg gas separator comprises, in combination, a housing; a chamber in the housing of which chamber one wall comprises a filter material that is wetted by a liquid to be passed through the housing, and another wall comprises a filter material that is not wetted by the liquid passing through the housing, but in fact is liquid-repellent; an inlet in the housing for delivering fluid comprising gas and liquid to the chamber between the liquid-wetted and liquid-repellent filter materials; a liquid outlet in the housing on the opposite side of the liquid-wetted material; and a gas outlet in the housing on the opposite side of the liquid-repellent material. Both the liquid-wetted and the liquid-repellent materials preferably have a pore size less than about 0.3 micron, at which harmful micro-organisms cannot pass therethrough. The housing and associated parts of the separator are preferably made of plastic, and are bonded or fused together in a one piece construction.

An administration kit utilizing this type of gas separator device is described in U.S. Pat. No. 3,650,093 patented Mar. 27, 1972.

The filter in accordance with the present invention combines these multiple device systems into one, all included within a single housing. The filter in accordance with the invention comprises, in combination, a filter housing; a filter chamber in the housing; an inlet member and an outlet member in the housing in fluid flow communication with the filter chamber; a filter in the filter chamber disposed across the line of fluid flow through the chamber from the inlet member to the outlet member so that all through flow must pass through the filter, and dividing the chamber into two portions, one upstream and one downstream of the filter; a vent in the housing, in flow communication with the upstream portion of the filter chamber; and a liquid-impermeable gas-permeable porous member disposed across the line of flow through the vent, so that all vent flow must pass through the member, the member restricting such flow to gas to which it is permeable; the inlet member being shaped for attachment to a supply of intravenous liquid for intravenous administration; and the outlet member being shaped for attachment to an intravenous administration apparatus.

In the preferred embodiment, the inlet member is provided with a spike, for piercing a supply chamber made of plastic film and forming a liquid-tight seal therewith, and the outlet member is provided with a standard fitting, such as a spike socket, for attachment to an intravenous administration apparatus similarly equipped with a spike of other standard fitting that can enter the socket.

A preferred embodiment of the filter of the invention is illustrated in the drawings, in which:

FIG. 2 is a longitudinal sectional view, taken along the line 2—2 of FIG. 1; and FIG. 3 is a cross-sectional view, taken along the line 3—3 of FIG. 1.

Figure 1:
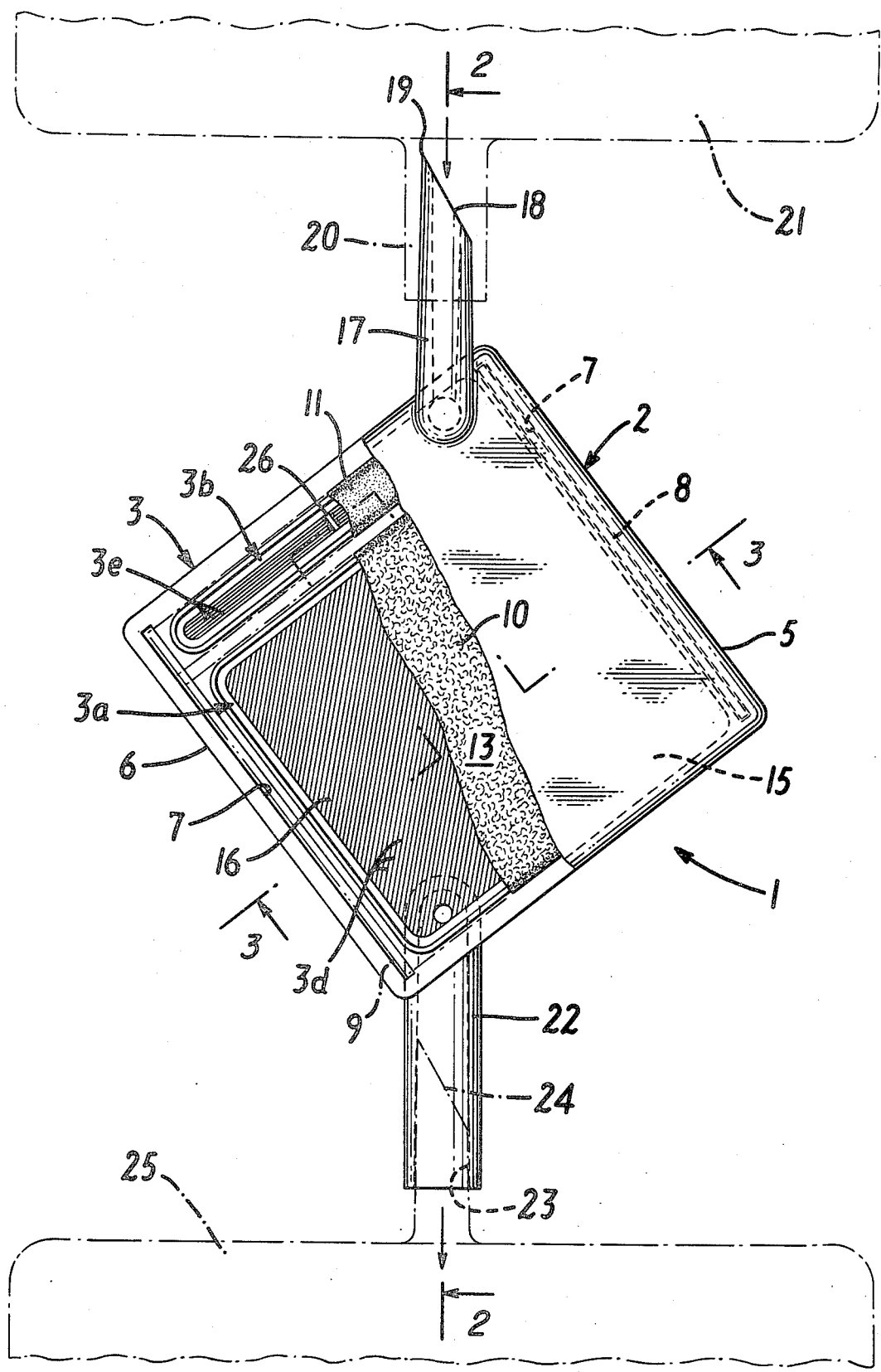
FIG. 1 represents a longitudinal section through a filter of the invention.

The housing can be of either a rigid or a flexible construction. Each type of construction has certain advantages. A rigid construction, using rigid sheets or molded or cast plastic parts or tubing, or parts or tubing made of metal, makes it possible for the device to resist high internal fluid pressures up to the bubble point of the filter used. The housing can also be made of flexible tubing or sheet material.

The housing can be transparent, in which case the functioning of the device and the condition of the filter can be observed without dismantling the device. The filter that is employed serves to remove both gaseous and suspended solid material, such as dirt and other contaminants, either of which could lead to filter blockage.

It will be evident from the above that the housing can be constructed of rigid or flexible plastic material that is also transparent, such as polyethylene, polypropylene, polymethyl methacrylate, polymethylacrylate, polymethyl penetene-1, polyvinyl chloride, and vinyl chloride-vinylidene chloride copolymers. Translucent materials such as polypropylene, polyethylene, urea-formaldehyde and melamine-formaldehyde polymers can also be employed. Other plastic materials that are suitable include polystyrene, polyamides, polytetrafluoroethylene, polychlorotrifluoroethylene, polycarbonates, polyesters, phenol-formaldehyde resins, polyvinyl butyral, cellulose acetate, cellulose acetate-propionate, ethyl cellulose, and polyoxymethylene resins.

Metal housings can be used. Suitable metals include stainless steel, aluminum, and stainless alloys, such as nickel, chromium, vanadium, molybdenum, and manganese alloys. The housing material should of course be inert to the fluids being processed.

The filter material is wetted preferentially by the liquid, and can have any desired pore size, according to the nature of the fluid being treated, and the nature of the contaminants, if any, to be removed. Since most filter materials are wetted by some liquids, and repel others, the materials chosen for the filter will depend upon the filter being processed.

In order to be effective in repelling and therefore not passing a gas, the liquid-wetted portion of the filter material should have a pore size of less than about 25 microns, and preferably less than about 3 microns.

In order to be effective in repelling and therefore not passing a liquid, the liquid-repellent porous member across the vent in the housing likewise should have a pore size of less than about 25 microns, and preferably less than about 3 microns. Thus, the same filter can easily serve as a substrate for both the filter and the porous member. For bacteria removal purposes, as previously indicated, the pore size should be less than about 0.3 micron, and preferably less than 0.2 micron. A filter material or porous member that has too large a pore size can have the pore size reduced by impregnation, or coating, or both, with particulate and/or fibrous material. Such materials and procedures are known.

Thus, there can be used as the liquid-repellent porous member woven or nonwoven textile materials made of cotton, jute, sisal, hemp, flax, linen, wood fiber, metal wire, such as stainless steel, copper and aluminum, plastic filaments (monofilaments and yarn) such as nylon, polyvinyl chloride, polyacrylonitrile, esters of terephthalic acid and ethylene glycol, cuprammonium rayon, acetate rayon, viscose rayon and polyvinylidene chloride, sintered composites made from metal powder or particles, such as stainless steel, copper, bronze, or monel, or from plastic particles, such as polyvinyl chloride, nylon, polyethylene, polypropylene, polytetrafluoroethylene, and polyfluorotrichloroethylene; glass and ceramic materials; papers of various types, made up of cellulose fibers, cellulose fluff, plastic fibers, such as polyvinyl chloride, cellulose acetate, polyvinylidene chloride, nylon, and any of the other plastic filaments mentioned above, taken singly or in any combination; and microporous sheets, such as synthetic resin and cellulose derivative membrane filters.

Impregnated and/or coated microporous filter sheet materials meeting these general requirements and that in particular can be made with less than 0.3 micron pores and thus are useful to prevent entry of harmful microorganisms include the microporous materials of U.S. Pat. Nos. 3,158,532 to Pall et al. dated Nov. 24, 1964; 3,238,056 to Pall et al. dated Mar. 1, 1966, 3,246,767 to Pall et al. dated Apr. 19, 1966, and 3,353,682 to Pall et al. dated Nov. 21, 1967. Also useful for this purpose are microporous ceramic filters and the microporous membrane filters described in U.S. Pat. Nos. 1,421,341 to Zsigmondy, 1,693,890 and 1,720,670 to Duclaux, 2,783,894 to Dovell, 2,864,777 to Robinson, and 2,944,017 to Cotton.

Liquid repellency in the porous member is obtained, if the member is of a material that is wetted by the liquid, by treatment of that portion of the material with a material that repels the liquid when disposed on the surfaces of the pore walls of the filter material. The repellant material can be applied from a solution or dispersion thereof, in a solvent or dispersant, which desirably includes a binder, to retain the repellent on the pore wall surfaces, unless the repellent is reactive therewith, and can bond itself thereto.

The application can be by printing, spraying, coating, impregnating, dipping, or by exposure to a vapor, such as that of a low boiling silicone compound. It is necessary to use a technique that results in thorough treatment of the entire length of the pores, from surface to surface of the filter material. This requires impregnation of the wall surfaces of the pores from end to end, best achieved by allowing the solution or dispersion of the repellent to flow into and through the pores in the treated zone, by capillarity or by pressure application.

It will be appreciated that in nonwoven substrates, such as paper, nonwoven bats, and microporous layers formed by laydown from a fluid dispersion, the through pores that extend from one surface to another are composed of interconnected pores which are the interstices between the particulate material of which the material is made.

The amount of repellent that is required depends upon the effectiveness of the material as a repellent, and the volume of pores being treated. Usually less than 25 percent by weight of the volume being treated and preferably from 0.025 percent to 15 percent by weight of the volume being treated is sufficient.

The repellent is chosen according to the liquid suspending medium being filtered. It must repel such liquid, or be rendered so in situ on the pore surface.

For a hydrophobic or water-repellent surface, there can be used silicone resins and silicone oils of the general type $R_n$—Si—O—Si—$R_n$, where n is 1 or 2. n is 1 in the case of the fluids, and n is 2 in the case of the solids, which contain crosslinks between chains. Mixtures containing species in which n is from 1 to 3 can also be used. R is a hydrocarbon group having from one to eighteen carbon atoms.

Also useful are the quaternary ammonium salt derivatives of silicone compounds described in U.S. Pat. No. 2,738,290, dated Mar. 31, 1956. These are substantive to cellulosic filter materials, as noted in the patent. Also, the hydrophobic oils and waxes can be used, in appropriate circumstances, where they can be made permanent.

If the filter material is liquid-repellent, and it is desired to make it liquid-wetted, it is advantageous to apply a liquid-wetting material thereto. The same treatment principles and proportions apply to liquid-wetted materials as to liquid-repellent materials. Typical wetting agents that are suitable are polyvinyl alcohol, alkyl aryl polyether alcohols, melamine formaldehyde resins, and the like. These wetting agents can be applied from a dispersion or emulsion. The vent and porous member that passes the gas being separated from the liquid is so placed in the housing that the gas can reach it. Inasmuch as gases normally rise, this means that at least a part of the liquid-repellent member is at an upper portion or wall of the housing. If the liquid-repellent material is confined to a lower portion of the housing, the air or the gas may not pass through it until an air pocket deep enough to reach the uppermost portion of the member has built up in the chamber. The building up of such a gas pocket is not a disadvantage, if the liquid-wetted filter material is still fully open to the passage of fluid, and is not covered by or immersed in the air or other gas pocket, but such a device may be position-sensitive. It is therefore less preferred, for some uses.

In its simplest construction, the filter element has a flat surface, or substantially so. However, in order to increase the surface area of the filter, for use in a limited space, the filter can be curved, bowed inwardly against flow or outwardly in the direction of flow, and it also can be corrugated. The filter can extend straight across the two outlets, if they are in-line, or in a Y-configuration, or it can be bent, say, in an L-shape, if the outlets are at right angles to each other, as in a T-housing, or in an in-line housing with the gas outlet in a wall of the through passage, upstream of the outlet. The filter can also be tubular, and extend all the way around the wall of the through passage in the liquid repellent portion, and have a liquid-wetted tip portion extending across the passage, as in a thimble.

For simplicity of construction, the housing is best formed in two or three matching pieces, which when assembled define the connected through passages, inlet and outlets, with the liquid-repellent filter material fixed across the gas outlet, and the liquid-wetted filter material fixed across the liquid outlet, and preferably parts of the same filter element. These parts can be separately molded, and then attached together, by bolts, or by heat-fusing, or by solvent-or adhesive-bonding. In the case of plastic materials, solvent-bonding is a preferred attachment technique, because it eliminates the presence of extraneous adhesives, does not affect transparency at the joints of a transparent housing, and is also leakproof.

The housing parts are constructed so that the filter materials contained therein are attached to the walls thereof across from the inlet and/or outlets, so that all fluid must pass through some part of the filter before it can emerge from the housing. If there are two housing parts, one housing part has a gas outlet or vent on the outside of the liquid-repellent porous member, and the same housing part has a liquid outlet communicating with the space on the outside of the liquid-wetted filter material. The housing thus has at least three openings, the inlet, and two outlets, to which the fluid containing both gas and liquid is delivered, for separation of the gas therefrom and the opposite side of the liquid-repellent and liquid-wetted materials, respectively, being adapted to vent gas separated from the liquid, and to deliver liquid from which gas has been separated.

The device shown in the drawings illustrates one embodiment of this type of construction.

The filter assembly shown in FIGS. 1 to 3 has a housing 1 of transparent rigid or semirigid plastic material, such as polyvinyl chloride, polymethyl acrylate, polymethyl methacrylate, or polyvinylidene chloride, or of translucent material, such as polypropylene, polyethylene, or polyamide, or opaque, such as acrylonitrile-butadiene-styrene terpolymer, polystyrene, or polycarbonate. The housing is a flattened cube, in two portions 2,3. Each housing portion 2,3 is shallowly dished with outer peripheral flanges 5,6. Portion 3 has peripheral slots 7 on two sides and portion 2 has peripheral ribs 8 extending into the slots 7. Portion 2 also has ribs on the flanges 5, which are sacrifically integrated and thus bonded to housing portion 3 at flange 6 to form the completed housing such as, for example, by ultrasonic welding or by use of an adhesive or mutual solvent; these ribs are accordingly not shown.

The slots 7 are deep enough to receive the end portions 9 of the filter sheet 10, and permit the flanges 5,6 to be integrated together without interference by the edges 9.

The edges 9 of the filter sheet 10 are held in a fluid-tight seal to the portion 3 on the outer side of slots 7, and the filter sheet extends from end to end and side to side of the major part 3a of portion 3. The filter sheet 10 is liquid-wetted, and can for example be a microporous hydrophilic nylon membrane. Beside the sheet 10 and in the same plane, but extending only over part 3b of portion 3, is a liquid-repellent gas-permeable sheet 11, such as an expanded microporous polytetrafluoroethylene sheet. This sheet is also bonded to the portion 3 at its edges, in recess 3c.

The housing part 3a is ribbed, the ribs 3d extending diagonally across that part, while the part 3b is also ribbed, the ribs 3e extending parallel to the long sides of part 3b.

The housing encloses a filter chamber 13 and since the entire peripheries of the sheets 10, 11 are sealed to the housing portion 3, the filter 10 and sheet 11 accordingly divide the filter chamber 13 into two portions, an upstream portion 15, and a downstream portion 16.

Opening into the upstream portion 15 is an inlet member 17 of generally tubular configuration, terminating in a spike 18 with a sharp tip 19 for penetration of the fitting 20 (shown in dashed lines) of a plastic reservoir or storage vessel 21 containing liquid for intravenous administration, and forming a leak-tight seal therewith when penetrated into the vessel.

The downstream portion 16 of the filter chamber is provided with an outlet member 22, also generally of tubular configuration, and terminating in a socket 23, for reception of the corresponding spike 24 of an intravenous liquid administration kit 25, shown in dashed lines. Thus, liquid entering through the inlet member 17 must pass through the filter 10 in order to reach the outlet member 22 and the administration kit 25.

Penetrating through the wall of the housing portion 3 and opening into part 3b is a vent 26, closed off by liquid-repellent gas-permeable filter sheet 11. Since this sheet is not wetted by the intravenous liquid being administered, since this is an aqueous fluid which wets hydrophilic materials but not hydrophobic materials, the pores of the polytetrafluoroethylene sheet are not penetrated by liquid, and therefore remain open for passage of gas therethrough at all times, which can accordingly escape via vent 26 from the housing.

In contrast, the pores of the filter 10 are saturated with liquid, immediately that liquid fills the upstream chamber 15, with the result that under gravity flow administration, as shown, the filter 10 is not penetrated by gas, but blocks the passage of gas therethrough. As a result, any gas entering with the liquid through the inlet cannot pass through the filter 10, but since it can pass through the sheet 11, it escapes through the vent 26.

It will be noted that the spike 18 and socket 23 are at opposite corners of the housing 1. This means that the device when installed assumes a position in which the sheet 11 extends diagonally upward, and so is in a position to vent via vent 26 all gas rising to the top of chamber 15, aided by the ribs 3e. The ribs 3d are thus vertical, aiding in guiding liquid to outlet 22.

Thus, in operation, after the spike 18 of the filter assembly has been pushed into the liquid supply vessel at 20, as illustrated, liquid flows freely into the upstream chamber 15, passes through the filter 10, and then enters the downstream chamber 16, whence it passes along the ribs 3d and leaves through the outlet member 22 and the socket 23 into the intravenous administration kit 25, where it is administered. Gas blocked from passage through the filter 10 escapes through the vent 26 via the liquid-repellent sheet 11.

The filter assembly shown in the drawings are described above is useful to separate gases from liquids and to filter intravenous liquids in any type of medicinal and chemical application. It can, for instance, be used both to clear a line of air and to prevent the introduction of air and contaminants into a patient receiving an injection of any type of fluid medicament, such as a parenteral fluid, blood transfusions, blood plasma, intravenous feeding solutions, and the like. Such fluids can be delivered to a patient under gravity pressure, or under higher pressures, such as are encountered when the fluid delivery is effected by means of a syringe pump, and will prevent the introduction of air into the patient, at all pressures below the bubble point of the liquid-wetted filter material that is used, both at the beginning of the introduction of the liquid, even when the line before the line before the separator contains air, and after delivery of fluid has exhausted the supply.

Having regard to the foregoing disclosure, the following is claimed as the inventive and patentable embodiments thereof:

1. A filter for gravity-feed intravenous liquid administration, comprising a plastic filter housing in at least two generally rectilinearly shaped portions bonded together and defining a filter chamber therebetween; an inlet member located generally at a first corner of said housing and an outlet member located generally at a second corner of said housing diagonally opposite said first corner in fluid flow communication with the filter chamber, the inlet member being arranged to be oriented up when so installed for gravity feed of intravenous liquid from the supply, with the outlet member down; a liquid-permeable filter that is gas-impermeable when filled with liquid disposed in the filter chamber across the line of gravity-feed fluid flow through the chamber from the inlet member to the outlet member so that all through flow must pass through the filter, and extending vertically when the pointed member is oriented up; the chamber being divided into two vertically-extending portions, one upstream and one downstream of the filter; a vent in an uppermost portion of the housing when the pointed member is oriented up, in flow communication with the upstream portion of the filter chamber; and a liquid-impermeable gas-permeable porous member extending vertically when the pointed member is oriented up and disposed above the filter across the line of flow through the vent, so that all vent flow must pass through the member, the member passing to the vent flow gas rising to the top of the upstream portion of the filter chamber and restricting such flow to gas to which it is permeable; the inlet member being shaped for attachment to a supply of liquid for intravenous administration; and the outlet member being shaped for attachment to an intravenous liquid administration apparatus, the upper walls of the filter chamber on the upstream side of the filter being arranged to funnel gas rising in the chamber towards the inlet member and vent, and to permit liquid flowing downwardly to spread out over the filter surface, the lower walls on the upstream side of the filter drawing inwardly towards the bottom of the chamber to maintain a uniform flow over the filter surface as the liquid diminishes in volume due to flow through the filter; and the lower walls of the filter chamber on the downstream side being arranged to funnel liquid flowing downwardly in the chamber towards the outlet member.

2. A filter according to claim 1, wherein the filter and porous member each have an average pore size less than about 0.3 micron.

3. A filter according to claim 1 wherein the housing and associated parts are made of transparent plastic.

4. A filter according to claim 3, wherein the housing and any other plastic parts are bonded or fused together in a one-piece construction.

5. A filter according to claim 1, in which the inlet member comprises a spike for piercing a wall of an intravenous liquid supply vessel.

6. A filter according to claim 1 wherein the porous member is a microporous membrane.

7. A filter according to claim 1 wherein the outlet member comprises a socket.

8. A filter according to claim 1 wherein the inner wall of the housing portion downstream of the filter is ribbed with upwardly and downwardly extending ribs to facilitate flow of liquid to the outlet.

* * * * *

UNITED STATES PATENT AND TRADEMARK OFFICE
CERTIFICATE OF CORRECTION

PATENT NO. : 4,177,149
DATED : December 4, 1979
INVENTOR(S) : David J. Rosenberg It is certified that error appears in the above—identified patent and that said Letters Patent is hereby corrected as shown below:

Column 2, line 45 : "liquid-gas" should be --liquid-wetted-- line 49 : "outlet" should be --outlets--

Column 3, line 22 : "elements" should be --element--

Column 4, line 16 : "of" should be --or--

Column 8, line 60 : "are" should be --as--

Signed and Sealed this

Eighth Day of July 1980

[SEAL]

Attest:

SIDNEY A. DIAMOND

Attesting Officer

Commissioner of Patents and Trademarks